United States Patent [19]

Ibsen et al.

[11] Patent Number: 4,859,716

[45] Date of Patent: Aug. 22, 1989

[54] MICROFILLED DENTAL COMPOSITE AND METHOD FOR MAKING IT

[75] Inventors: Robert L. Ibsen, Santa Maria; William R. Glace, Orcutt, both of Calif.

[73] Assignee: Den-Mat Corporation

[21] Appl. No.: 118,154

[22] Filed: Nov. 6, 1987

[51] Int. Cl.$^4$ .......................... C08J 3/28; C08K 3/36; A61K 6/08

[52] U.S. Cl. .......................... 522/14; 522/28; 522/83; 522/181; 523/116

[58] Field of Search .................. 522/14; 523/117, 116

[56] References Cited

U.S. PATENT DOCUMENTS

| | | | |
|---|---|---|---|
| 4,297,266 | 10/1981 | Ibsen et al. | 523/117 |
| 4,674,980 | 1/1987 | Ibsen et al. | 522/14 |

Primary Examiner—John C. Bleutge
Assistant Examiner—Susan Berman
Attorney, Agent, or Firm—Owen, Wickersham & Erickson

[57] ABSTRACT

A microfilled dental composite containing from about 30% to about 60% filler. The filler being sub-micron hydrophobic silica particles of about 0.01–0.04 micrometers in diameter. The filler is dispersed in ethoxylated bisphenol A dimethacrylate resin containing suitable aliphatic dimethacrylate diluents up to about 40% by weight and curing agents effecting curing.

9 Claims, No Drawings

MICROFILLED DENTAL COMPOSITE AND METHOD FOR MAKING IT

This invention relates to a microfilled dental composite and to a method employing it.

BACKGROUND OF THE INVENTION

Heretofore the fillers in dental composites have been composed of particles from about 0.56 micron to about 150 microns in diameter. These relatively large particles have resulted in a rougher type of finish than many practitioners desired. Yet, although some manufacturers used a small amount of submicron filler particles, which are typically 0.02 to 0.04 micron in diameter (to eliminate settling, for example), they have used them only up to about 5% by weight of the composite, and most of the particles remained relatively large.

Recently, various manufacturers have placed on the market "microfilled" composites in which *all* of the filler was in the 0.02 to 0.04 micron range, and a smoother finish was thereby obtained. However, when using these small particle fillers, only about 25% to 50% of the composite could be filler.

When such a relatively small percentage of filler was added to the typical dental resin, the result was that physical properties, such as tensile strength and water sorption, were severely compromised.

SUMMARY OF THE INVENTION

The present invention provides a microfilled dental composite containing from about 30% to about 60% filler, said filler being sub-micron hydrophobic silica particles of about 0.01–0.04 micrometers in diameter. The filler is dispersed in a resin, the main component of which is ethoxylated bisphenol A dimethacrylate, with suitable aliphatic dimethacrylate diluents up to about 40% by weight. Curing agents are added to effect a one-component light-cured restorative or a two-component self-cured material. A three-part curing system can be used to produce a two-component light-cured material with infinite cure, as in U.S. Pat. No. 4,297,266, issued Oct. 27, 1981 to Ibsen, et al.

The resultant cured material exhibits the smooth finish of a microfilled restorative, but has physical properties in the same range as conventional "small particle" restorative.

EXAMPLES OF PREFERRED EMBODIMENTS

The system is preferably a single, light-cured paste which is applied, shaped, etc. by the dentist, then cured by exposure to a special dental curing light.

EXAMPLE 1

A formulation system embodying this invention comprises the following illustrative ranges:

| Component | Parts by Weight |
|---|---|
| Ethoxylated bisphenol A dimethacrylate | 67.75–36.00 |
| Triethylene glycol dimethacrylate | 11.00–16.94 |
| Anti-oxidant (e.g., butyl hydroxy toluene) | 0.002–0.02 |
| Curing agent (e.g., 2,3-Bornanedione) | 0.05–0.20 |
| Cure accelerator (e.g., Ethyl-4-dimethylamino benzoate) | 0.05–0.20 |
| Sub-micron hydrophobic silica particles | 15.00–55.00 |

The submicron hydrophobic silica may be Degussa's Aerosil R 972 which has a particle range of 0.01 to 0.04 microns, with an average particle size of approximately 0.02 micron ($20 \times 10^{-7}$ cm). The basis for the manufacture of hydrophobic silica is a very pure form of silicon dioxide aerosol obtained by flame hydrolysis. Its particles vary in diameter between 10 and 40μ. On each 100 sq. meters of surface area, it has about 0.5 millimol silanol groups; hence it is hydrophilic. On its surface, there is a one silanol group per 28–33 $Å^2$ (—Si—OH). Hence, with 200 square meters per gram specific surface area, there are about $6.2 \times 10^{20}$ silanol groups per gram, i.e., one millimol. This gives a figure of about 2000 silanol groups per particle.

In a continuous process, some 75% of these silanol groups can be chemically reacted with dimethyl dichlorosilane, the resultant product having about 0.7 millimol of chemically combined methyl groups per 100 square meters of surface area. The silica when thus reacted becomes hydrophobic and behaves differently in organic liquids from the hydrophilic material. For this purpose, freshly obtained hydrophilic silica is separated from the bulk of the hydrochloric acid formed in the flame hydrolysis. Then, this silica, dimethyl dichlorosilane, and steam are pneumatically fed in parallel flow into a fluidized bed reactor heated to about 400° C. by means of an inert gas such as nitrogen. Besides the chemical reaction of the chlorosilane with the silanol groups of the surface, the desorption of the hydrochloric acid resulting from the reaction takes place in the reactor in a continuous stream, so that there is an analytically assessable chlorine content of below 0.03%. The main quantity of hydrochloric acid is removed from the freshly manufactured $SiO_2$ and the material does not yet contain any absorbed water. Moreover, siloxane bridges still exist on the surface of the particles, these having formed at the high temperatures used in the process. These bridges break up in the presence of water vapor and chlorosilane in the reaction zone, whereupon the reaction can take place in the nascent state of the silanol group formation.

Analytical data and moisture absorption data of hydrophobic silica are given in Tables 1 and 2 respectively.

TABLE 1

| Analytical Data on Hydrophobic AEROSIL R 972 | |
|---|---|
| $SiO_2$ + (—$CH_3$) | 99.8% |
| Surface area (acc. to Bruneuer, Emmet & Teller) | 120 ± 30 $m^2/g$ |
| Average particle size | 20 ± $10^{-7}$ cm |
| Carbon | 1.1 ± 0.2% |
| pH value (4% dispersion methanol/water 1:1) | 3.8 ± 0.2% |
| Chlorine content | 0.04 ± 0.01% |
| Heavy metals | 0.003% |
| As | 0.0001% |
| $Fe_2O_3$ | 0.003% |
| $Al_2O_3$ | 0.05% |
| $TiO_2$ | 0.03% |
| $Na_2O$ | 0.01% |
| Bulk density | about 40–60 g/l |
| Compacted volume | about 10 ml/g |

TABLE 2

| Relative air humidity in % | Moisture Absorption in mg/100 m$^2$ | | | |
|---|---|---|---|---|
| | 20 | 40 | 60 | 80 |
| Hydrophilic silica | 1.3 | 4.0 | 10 | 30 |
| Hydrophobic silica | 0.3 | 0.4 | 0.9 | 1.5 |

2,3-Bornanedione and Ethyl-4-dimethyl amino benzoate are exiplex-forming photo initiators. Other suitable photo initiators include:

2,3-Bornanedione with ethyl-2-dimethyl amino benzoate
Benzil with ethyl-4-dimethyl amino benzoate
Benzil with ethyl-2-dimethyl amino benzoate
2-Isopropyl thioxanthone with ethyl-4-dimethyl amino benzoate
2-Isopropyl thioxanthone with ethyl-2-dimethyl amino benzoate
Dibenzyl ketone with ethyl-4-dimethyl amino benzoate
Dibenzyl ketone with ethyl-2-dimethyl amino benzoate
2-Hydroxy-2-methyl-1-phenyl-propan-1-one with ethyl-2-dimethyl amino benzoate
2-Hydroxy-2-methyl-1-phenyl-propan-1-one with ethyl-4-dimethyl amino benzoate
Benzil dimethyl acetal with ethyl-4-dimethyl amino benzoate
Benzil dimethyl acetal with ethyl-2-dimethyl amino benzoate
Dimethoxy acetophenone with ethyl-4-dimethyl amino benzoate
Dimethoxy acetophenone with ethyl-4-dimethyl amino benzoate
Benzoin methyl ether with ethyl-4-dimethyl amino benzoate
Benzoin methyl ether with ethyl-2-dimethyl amino benzoate.

EXAMPLE 2

A light-cured paste was made as follows:
Ethoxylated bisphenol A dimethacrylate: 80.00 pbw
Triethylene glycol dimethacrylate: 20.00
Butylated hydroxytoluene: 0.0125
2,3-Bornanedione: 0.18
Ethyl-4-dimethyl amino benzoate: 0.18
Sub-micron hydrophobic silica: 50.00

This paste was compared with one excellent non-microfilled dental composite and with two competing microfilled composites. The test results are shown in Table 3.

TABLE 3

| | Tensile Strength (psi) | Cure Shrinkage (%) | Thermal Expansion (ppm/°C.)* | Water Sorption (mg/cm$^2$) | Water Stability |
|---|---|---|---|---|---|
| An excellent non-microfilled dental composite | 7000 | 0.50 | 17 | 0.45 | Excellent |
| The dental composite of this invention | 6114 | 0.71 | 29 | 0.47 | Excellent |
| 1st competing microfilled composite (Silux) | 3890 | 1.29 | 55 | 1.33 | Poor |
| 2nd competing microfilled composite (Durafil) | 3485 | 1.16 | 62 | 1.05 | Medium |

*Over range of 5° to 55° C.

As these tests show, the tensile strength of the dental composite of this invention is substantially greater than that of the two competing microfilled composites and almost equal to that of an excellent non-microfilled composite. The cure shrinkage is lower than that of any of the microfilled composites. Thermal expansion is not much greater than that of the tested non-microfilled composite and much less than that of any of the microfilled composite. Water sorption is equal to that of the non-microfilled composite and very much less than that of the competing microfilled composites. Furthermore, color stability is excellent.

Water sorption with the system is below 0.5 mg/cm$^2$, even with only 30% filler. It remains low throughout the filler range at every concentration tested up to 55% total filler.

EXAMPLE 3

Two pastes were prepared as followed:

Paste A

Ethoxylated bisphenol A dimethacrylate: 80.00 pbw
Triethylene glycol dimethacrylate: 20.00
Butylated hydroxytoluene: 0.0125
Benzoyl Peroxide: 1.50
Sub-micron hydrophobic silica: 50.00

Paste B

Ethoxylated bisphenol A dimethacrylate: 80.00 pbw
Triethylene glycol dimethacrylate: 20.00
Butylated hydroxytoluene: 0.0125
2-hydroxy ethyl p-toluidine: 4.25
Sub-micron hydrophobic silica: 50.00

These pastes comprised a "self-cured" version of the present invention. When these two parts were mixed together, the material cured in 2½ minutes and exhibited the following properties:
Tensile strength: 6100 psi
Water sorption: 0.47
Thermal Expansion: 29 ppm/°C.

EXAMPLE 4

Two pastes were prepared as followed:

Paste A

Ethoxylated bisphenol A dimethacrylate: 80.00 pbw
Triethylene glycol dimethacrylate: 20.00
Butylated hydroxytoluene: 0.0125
Benzoyl Peroxide: 0.55
Sub-micron hydrophobic silica: 50.00

Paste B

Ethoxylated bisphenol A dimethacrylate: 80.00 pbw
Triethylene glycol dimethacrylate: 20.00
Butylated hydroxytoluene: 0.0125
2,3-Bornanedione: 0.18
Ethyl-4-dimethyl amino benzoate: 20.00
Sub-micron hydrophobic silica: 50.00.

When these two parts were mixed together in equal portions, they did not react; however, when activated with a dental curing unit, the material hardened immediately to a depth of about 3½ mm. The material was placed in the absence of light for one hour and again checked for depth of cure. Cure had extended to the depth of the sample, i.e., 12 mm.

This example illustrates the use of the present invention in the form of a continuous cure two-part system.

EXAMPLE 5

A paste was prepared as follows:
Ethoxylated bisphenol A dimethacrylate: 67.75 pbw
Triethylene glycol dimethacrylate: 16.94
Butylated hydroxytoluene: 0.02
2,3-Bornanedione: 0.20
Ethyl-4-dimethyl amino benzoate: 0.20
Sub-micron hydrophobic silica: 15.00.

When exposed to a dental curing light for 30 seconds, the material cured to a depth of 5.35 mm, and had a tensile strength of 5800 psi.

EXAMPLE 6

A pste was prepared as followed:
Ethoxylated bisphenol A dimethacrylate: 36.00 pbw
Triethylene glycol dimethacrylate: 11.00
Butylated hydroxytoluene: 0.002
2,3-Bornanedion: 0.05
Ethyl-4-dimethyl amino benzoate: 0.05
Sub-micron hydrophobic silica: 55.00.

When exposed to a dental curing light for 30 seconds, the material cured to a depth of 4.85 mm, and had a tensile strength of 7800 psi.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A microfilled dental composite containing from about 30% to about 60% filler, said filler being sub-micron hydrophobic silica particles of about 0.01–0.04 micrometers in diameter, dispersed in ethoxylated bisphenol A dimethacrylate resin containing suitable aliphatic dimethacrylate diluents up to about 40% by weight and curing agents effecting curing.

2. The composite of claim 1 including means for effecting a one-component light-cured material.

3. The composite of claim 1 containing a two-component self-cured material.

4. The composite of claim 1 in the form of a single, light-cured paste that is applied, and shaped and then cured by exposure to a dental curing visible light.

5. A microfilled dental composite, comprising:

| Component | Parts by Weight |
|---|---|
| Ethoxylated bisphenol A dimethacrylate | 67.75–36.00 |
| Triethylene glycol dimethacrylate | 11.00–16.94 |
| Anti-oxidant (e.g., butyl hydroxy toluene) | 0.002–0.02 |
| Curing agent | 0.05–0.20 |
| Cure accelerator | 0.05–0.20 |
| Sub-micron hydrophobic silica particles | 15.00–55.00 |

6. The composite of claim 5 wherein the sub-micron hydrophobic silica has a particle range of 0.01 to 0.04 microns, with an average particle size of approximately 0.02 micron ($20 \times 10^{-7}$ cm) and is based on hydrophobic very pure silicon dioxide aerosol obtained by flame hydrolysis, the particles varying in diameter between 10 and 40μ having on each 100 sq. meters of surface area about 0.5 millimol silanol groups so that it is hydrophilic and on its surface, one silanol group per 28–33 Å$^2$ (—Si—OH) so that with 200 square meters per gram specific surface area, there are about $6.2 \times 10^{20}$ silanol groups per gram, i.e., one millimol and therefrom about 2000 silanol groups per particle.

7. The composite of claim 5 wherein the curing agent is 2,3-bornanedione and ethyl-4-dimethyl amino benzoate.

8. The composite of claim 5 wherein the curing agents and cure accelerators are chosen from the following pairs:
2,3-Bornanedione with ethyl-2-dimethyl amino benzoate
Benzil with ethyl-4-dimethyl amino benzoate
Benzil with ethyl-2-dimethyl amino benzoate
2-Isopropyl thioxanthone with ethyl-4-dimethyl amino benzoate
2-Isopropyl thioxanthone with ethyl-2-dimethyl amino benzoate
Dibenzyl ketone with ethyl-4-dimethyl amino benzoate
Dibenzyl ketone with ethyl-2-dimethyl amino benzoate
2-Hydroxy-2-methyl-1-phenyl-propan-1-one with ethyl-2-dimethyl amino benzoate
2-Hydroxy-2-methyl-1-phenyl-propan-1-one with ethyl-4-dimethyl amino benzoate
Benzil dimethyl acetal with ethyl-4-dimethyl amino benzoate
Benzil dimethyl acetal with ethyl-2-dimethyl amino benzoate
Dimethoxy acetophenone with ethyl-4-dimethyl amino benzoate
Dimethoxy acetophenone with ethyl-4-dimethyl amino benzoate
Benzoin methyl ether with ethyl-4-dimethyl amino benzoate
Benzoin methyl ether with ethyl-2-dimethyl amino benzoate.

9. A dental composite consisting essentially of: a light-cured paste as follows:
Ethoxylated bisphenol A dimethacrylate: 80.00 pbw
Triethylene glycol dimethacrylate: 20.00
Butylated hydroxytoluene: 0.0125
2,3-Bornanedione: 0.18
Ethyl-4-dimethyl amino benzoate: 0.18
Sub-micron hydrophobic silica, particle size range 0.01–0.04 microns: 50.00.

* * * * *